United States Patent [19]

Ceschel et al.

[11] Patent Number: 5,124,315
[45] Date of Patent: Jun. 23, 1992

[54] LIQUID PHARMACEUTICAL COMPOSITION FOR NASAL ADMINISTRATION CONTAINING A POLYPEPTIDE AS ACTIVE INGREDIENT

[75] Inventors: Giancarlo Ceschel; Antonella M. Segu'; Celestino Ronchi, all of Milan, Italy

[73] Assignee: Phideatech S.R.L., Milan, Italy

[21] Appl. No.: 716,390

[22] Filed: Jun. 17, 1991

[51] Int. Cl.⁵ .............................. A61K 37/02
[52] U.S. Cl. ............................ 514/12; 514/2; 514/530; 514/307; 514/3; 514/4; 514/15; 514/800; 514/808; 424/719
[58] Field of Search ............ 514/12, 2, 3, 4, 15, 514/808, 800; 424/719, 85.9, 85.8; 530/307

[56] References Cited

U.S. PATENT DOCUMENTS

| | | | |
|---|---|---|---|
| Re. 32,919 | 5/1989 | Sarnoff | 424/719 |
| 4,466,960 | 8/1984 | Silverman et al. | 424/719 |
| 4,476,116 | 10/1988 | Anik | 514/15 |
| 4,772,585 | 9/1988 | Sarnoff et al. | 424/719 |
| 4,900,730 | 2/1990 | Miyalechi | 514/12 |
| 4,985,242 | 1/1991 | Sekine et al. | 514/12 |
| 5,010,056 | 4/1991 | Boghen et al. | 514/12 |
| 5,015,626 | 5/1991 | Christian et al. | 514/12 |
| 5,015,627 | 5/1991 | Lindsey et al. | 514/12 |
| 5,026,546 | 6/1991 | Hilgers et al. | 514/12 |

FOREIGN PATENT DOCUMENTS

| | | | |
|---|---|---|---|
| 0067513 | 12/1982 | European Pat. Off. | |
| 0363876 | 4/1990 | European Pat. Off. | |
| 0130961 | 8/1982 | Japan | 530/326 |

Primary Examiner—John Doll
Assistant Examiner—T. D. Wessendorf
Attorney, Agent, or Firm—Oblon, Spivak, McClelland, Maier & Neustadt

[57] ABSTRACT

A liquid composition for nasal administration of polypeptide/s containing ammonium tartrate and a buffer together with optional adjuvants.

7 Claims, No Drawings

LIQUID PHARMACEUTICAL COMPOSITION FOR NASAL ADMINISTRATION CONTAINING A POLYPEPTIDE AS ACTIVE INGREDIENT

The present invention relates to a liquid pharmaceutical composition for the nasal administration containing one or more polypeptides as active ingredients.

It is known that many polypeptides, both of natural and synthetic origin, and derivatives thereof are administered in various dosage forms, said forms comprising liquid or solid nasal spray form.

The majority of the liquid nasal spray pharmaceutical compositions contain, besides one or more polypeptides dissolved in a solvent such as water, also an absorption enhancing agent and a buffer to keep the pH of the solution at a physiologically acceptable value, that is at the same time compatible with the nature of the polypeptide, together with other optional adjuvants.

As absorption enhancing agents, there are known aromatic carboxyl acids and the ester and amide derivatives thereof, aminoacids, hydroxycarboxylic and polycarboxylic acids, salicylic acids and derivatives thereof, glycirrhizinates, surfactant agents, chelating agents.

Nasal spray compositions of the above mentioned types are described, for example, in the following documents: EP-A-115627, BE 897904, EP-A-183527, GB 2127689, JP 294737, EP-A-308725, EP-A-249811, EP-A-067513, EP-A-327756 (corresponding to FR-A-2623090), JP-A-1230530 and U.S. Pat. No. 4,476,116.

Tests conducted by the present inventors, have shown that the polypeptides can reach satisfactory and suitable haematic concentrations even without an absorption enhancing agent, and this observation is confirmed by what is taught in EP-A-363876, wherein a liquid composition for the nasal administration of a polypeptide merely containing an isotonic agent as adjuvant shows AUC (Area Under Curve) data superimposable with the ones of a similar composition also containing a known absorption enhancing agent. Furthermore, the same document underlines the undesired effects of some absorption enhancing agents (see page 2, lines 36-38).

An important problem connected with the use of liquid compositions of polypeptides, either with or without an absorption enhancing agent, concerns the stability of such active ingredients as being very prone to degrade, particularly in liquid environment.

Said drawback is recognized in literatures: see, for example U.S. Pat. No. 4,613,500 and EP-A-193372. Such specifications aim to overcoming the stability problems of liquid nasal sprays suggesting the use of powder nasal spray compositions that, however, still exhibit stability and nasal mucose irritation problems due to the presence of water-absorbing, insoluble dispersing agents that are employed to assist the active ingredient in the absorption. Moreover, the powder form can provide for a diffuse, efficient administration of the active ingredient only if this is micronized at differentiated particle size. To this purpose the above-mentioned U.S. Pat. No. 4,613,500 and EP-A-193372 use the active ingredients in form of powders comprising mixtures of particles exhibiting different diameters (10 to 250 microns) to provide for a fast absorption of the particles having a diameter of about 10 microns, and a delayed absorption as well due to the particles having a larger diameter to the purpose of maintaining a sufficient plasma concentration for a period of time. It is apparent that the manufacture of said powders having a very fine differentiated particle size is highly complicated and expensive.

The present inventors have accordingly conducted extensive researches for finding a suitable stabilizing agent. A number of compounds have been tested to check their stabilizing activity on liquid compositions containing polypeptides: at a certain point, it has been noticed that the majority of the tested compounds were already mentioned as additives for similar compositions in literature, such as U.S. Pat. No. 4,476,116, where the same compounds are used as absorption enhancing agents. Consequently, the tests have been prosecuted by making use of just the compounds of said U.S. Patent. However, the results of the tests effected were quite discouraging. In fact, such "absorption enhancing agents" were unable to assure a suitable stability of the polypeptide active ingredients.

It has been surprisingly found that only ammonium tartrate is a satisfactory stabilizing agent for liquid nasal compositions containing polypeptides as active ingredient. All of the other tested compounds including those disclosed as adjuvants in the prior art, are ineffective to improve the stability of polypeptide in liquid solutions under the conditions being in the common practice appropriate for storing this kind of products.

Accordingly the present invention relates to a liquid pharmaceutical composition for nasal administration comprising, as active ingredient, at least a natural or synthetic polypeptide or a derivative thereof, having a molecular weight of from 300 to 300,000, together with a physiologically compatible buffer in a suitable amount for the pH of the solution to remain in the range of from 3.5 to 7.0, such compositions being characterized by the fact that it contains ammonium tartrate at a concentration of from about 0.01 to about 2% w/w, as stabilizing agent.

Such composition is able to guarantee long stability and good absorption of the active ingredient, thereby avoiding the use of irritant absorption enhancing agents or complicated preparation and delivery techniques.

Also, such composition can optionally comprise an isotonic-making agent of from 0.01 to 0.9% w/w, and a preservative selected from the group comprising methyl p-hydroxybenzoate (0.01–0.15% w/w), propyl p-hydroxybenzoate (0.01–0.15% w/w) and sodium merthiolate (at a concentration of not higher than 0.01% w/w). Said preservative is used in the composition when this is not prepared and packaged in a sterile environment.

The above stated range of ammonium tartrate concentration was chosen in view of the following considerations. Ammonium tartrate is effective as stabilizing agent even at low concentration close to the lower limit stated above, and any further addition of ammonium tartrate over the upper limit of 2% not only does not increase its stabilizing activity, but it can cause toleration problems too.

The polypeptides that can be administered by means of the pharmaceutical composition according to the invention are selected from the group comprising calcitonin, insulin, luteinizing hormone releasing factor, interferons, protyrelin, somatotropin, parathormone, human natriuretic atrial hormone, desmopressin, oxytocin, vasopressin and their analogs or chemically modified derivatives. Preferably, the composition according to the invention contains calcitonin as the active ingredient.

The following examples are provided for illustrative purposes only, and are not intended as limiting the invention.

| EXAMPLE 1 | |
|---|---|
| Salmon calcitonin | 55000 I.U. |
| Ammonium tartrate | 600 mg |
| Citric acid, anhydrous | 655 mg |
| Sterile degassed water q.s. to | 100 ml |

| EXAMPLE 2 | |
|---|---|
| Salmon calcitonin | 55000 I.U. |
| Ammonium tartrate | 600 mg |
| Citric acid, anhydrous | 655 mg |
| Sodium merthiolate | 10 mg |
| Sterile degassed water q.s. to | 100 ml |

| EXAMPLE 3 | |
|---|---|
| Salmon calcitonin | 55000 I.U. |
| Ammonium tartrate | 600 mg |
| Citric acid, anhydrous | 344.5 mg |
| Sodium chloride | 500 mg |
| Sodium merthiolate | 10 mg |
| Sterile degassed water q.s. to | 100 ml |

| EXAMPLE 4 | |
|---|---|
| Salmon calcitonin | 55000 I.U. |
| Ammonium tartrate | 309.5 mg |
| Citric acid, anhydrous | 304.5 mg |
| Methyl p-hydroxybenzoate | 80 mg |
| Propyl p-hydroxybenzoate | 20 mg |
| Sterile degassed water q.s. to | 100 ml |

| EXAMPLE 5 | |
|---|---|
| Salmon calcitonin | 55000 I.U. |
| Ammonium tartrate | 600 mg |
| Citric acid, anhydrous | 393 mg |
| Sodium chloride | 500 mg |
| Methyl p-hydroxybenzoate | 80 mg |
| Propyl p-hydroxybenzoate | 20 mg |
| Sterile degassed water q.s. to | 100 ml |

| EXAMPLE 6 | |
|---|---|
| Luteinizing hormone releasing factor | 110 mg |
| Glacial acetic acid | 610 mg |
| Sodium acetate trihydrate | 200 mg |
| Ammonium tartrate | 200 mg |
| Sodium chloride | 600 mg |
| Methyl p-hydroxybenzoate | 80 mg |
| Propyl p-hydroxybenzoate | 20 mg |
| Sterile degassed water q.s. to | 100 ml |

| EXAMPLE 7 | |
|---|---|
| Vasopressin | 25 U.I. |
| Citric acid, anhydrous | 360 mg |
| Sodium citrate | 415.5 mg |
| Ammonium tartrate | 200 mg |
| Sodium chloride | 600 mg |
| Methyl p-hydroxybenzoate | 80 mg |
| Propyl p-hydroxybenzoate | 20 mg |

| EXAMPLE 7 -continued | |
|---|---|
| Sterile degassed water q.s. to | 100 ml |

| EXAMPLE 8 | |
|---|---|
| Desmopressin | 25 U.I. |
| Glacial acetic acid | 610 mg |
| Sodium acetate trihydrate | 200 mg |
| Ammonium tartrate | 200 mg |
| Sodium chloride | 600 mg |
| Methyl p-hydroxybenzoate | 80 mg |
| Propyl p-hydroxybenzoate | 20 mg |
| Sterile degassed water q.s. to | 100 ml |

It can be seen that in some of the foregoing Examples citric acid is mentioned: it is however to be noted that citric acid was not used as an absorption enhancing agent, but it is merely the acidic component of the buffer.

STABILITY TESTS

The stability of the formulation of example 1 has been evaluated against the following preparation:

| Comparison formulation | |
|---|---|
| Calcitonin | 55000 I.U. |
| Sodium chloride | 700 mg |
| Sodium citrate dihydrate | 618.5 mg |
| Citric acid, anhydrous | 609 mg |
| Benzalkonium chloride | 22 mg |
| Sterile degassed water q.s. to | 100 ml |

The tests have been carried out by HPLC titration under the following conditions:

Reagents

Ammonium phosphate, dibasic, R

Phosphoric acid, R

Acetonitrile, HPLC grade

Tetrahydrofurane, HPLC grade

Solvent buffer: thoroughly weigh and dissolve 1 g of glacial acetic acid, 1 g of sodium acetate trihydrate, R, and 3.75 g of sodium chloride, R, into a 550 ml volumetric flask with water (pH=4.0).

Mobile Phase 0.2M dibasic ammonium phosphate/acetonitrile/tetrhahydrofurane=720:260:20, adjusted to pH 5.3 with phosphoric acid, R grade.

Reference Substance

Salmon calcitonin working standard.

Apparatus

High pressure liquid chromatograph with variable wavelength UV detector, connected to a recorder and a computer.

Column: Whatman Partisphere Ca 5u (125×4) conditions

Column temperature: ambient

Flow rate: 1 ml/min

Detector: UV 220 nm

Injected amount: 10 ul

The results of the experiments are shown in Tables 1 and 2.

TABLE 1

Decrement values of the active ingredient calcitonin in the formulation of example 1.

| Time | 4° C. ± 1° C. ppm (%) | | 21° C. ± 1° C. ppm (%) | | 30° C. ppm (%) | |
|---|---|---|---|---|---|---|
| (zero) | 120.5 | (—) | | | | |
| 1 month | 120.8 | (100.2) | 121.8 | (101.1) | 117.2 | (97.1) |
| 45 days | 121.2 | (100.6) | 118.3 | (98.3) | 108.5 | (90) |
| 3 months | 120.3 | (99.8) | 115.8 | (96.1) | 105.2 | (87.3) |
| 6 months | 120.1 | (99.6) | 116.3 | (96.5) | 102.6 | (85.1) |
| 9 months | 119.7 | (99.3) | 114.8 | (95.2) | 101.4 | (94.1) |
| 12 months | 115.2 | (95.6) | 113.27 | (94.0) | 97.96 | (81.3) |
| 18 months | 113.27 | (94.0) | 111.7 | (92.7) | 89.7 | (74.0) |

TABLE 2

Decrement values of the active ingredient calcitonin in the comparison formulation.

| Time | 4° C. ± 1° C. ppm (%) | | 21° C. ± 1° C. ppm (%) | | 30° C. ppm (%) | |
|---|---|---|---|---|---|---|
| (zero) | 133.5 | (—) | | | | |
| 1 month | (—) | (—) | 129.7 | (97.1) | 118.2 | (88.4) |
| 3 months | (—) | (—) | 130.1 | (97.4) | 107.52 | (80.5) |
| 6 months | 129.2 | (96.7) | 115.9 | (86.8) | 101.2 | (75.2) |
| 9 months | 125.0 | (93.6) | 111.2 | (83.2) | (—) | (—) |
| 12 months | 125.2 | (93.8) | 106.9 | (80.1) | (—) | (—) |
| 18 months | 120.1 | (89.9) | 103.2 | (77.3) | (—) | (—) |

We claim:

1. A liquid pharmaceutical composition for nasal administration wherein the active ingredient consists of at least one polypeptide of a molecular weight ranging from 300 to 300,000, a physiologically acceptable buffer suitable to keep the solution pH in the range from 3.5 to 7.0, and a stabilizing agent consisting of ammonium tartrate at a concentration of from about 0.01 to about 2% w/w.

2. The composition as claimed in claim 1 in which the concentration of ammonium tartrate is between 0.01 and 0.15% w/w.

3. The composition as claimed in claim 1 further consisting of an agent that is suitable to make it isotonic, at a concentration of from 0.01 to 0.9% by weight of the total weight, and a preservative agent at a concentration of from 0.01 to 0.15% w/w.

4. The composition as claimed in claim 3 in which the isotonic-making agent is sodium chloride.

5. The composition as claimed in claim 3 in which the preservative agent is selected from the group consisting of methyl p-hydroxybenzoate, propyl p-hydroxybenzoate and sodium merthiolate.

6. The composition as claimed in claim 1 in which the polypeptide is selected from the group consisting of calcitonin, insulin, luteinizing hormone releasing factor, interferons, protyrelin, somatotropin, parathormone, human natriuretic atrial hormone, desmopressin, oxytocin, vasopressin, their analogs and chemically modified derivatives.

7. The composition as claimed in claim 6 in which the polypeptide is calcitonin.

* * * * *